US012728041B1

(12) United States Patent
Schumaier et al.

(10) Patent No.: US 12,728,041 B1
(45) Date of Patent: Sep. 8, 2026

(54) UNIVERSAL FITTING STRUCTURE FOR HEARING PROTECTION DEVICE

(71) Applicant: Daniel R Schumaier, Elizabethton, TN (US)

(72) Inventors: Daniel R. Schumaier, Elizabethton, TN (US); Seth Elkins, Johnson City, TN (US); Richard Trent, Jonesborough, TN (US); Mark A Neilson, Zimmerman, MN (US); Dale F Kundis, Oviedo, FL (US)

(73) Assignee: Daniel R. Schumaier, Elizabethton, TN (US)

(*) Notice: Subject to any disclaimer, the term of this patent is extended or adjusted under 35 U.S.C. 154(b) by 0 days.

(21) Appl. No.: 19/440,711

(22) Filed: Jan. 6, 2026

(51) Int. Cl.
*A61F 11/08* (2006.01)
*H04R 1/10* (2026.01)

(52) U.S. Cl.
CPC .......... *A61F 11/085* (2022.01); *H04R 1/1016* (2013.01); *H04R 1/1041* (2013.01); *H04R 1/1058* (2013.01); *H04R 1/1083* (2013.01); *A61F 2240/001* (2013.01)

(58) Field of Classification Search
None
See application file for complete search history.

(56) References Cited

U.S. PATENT DOCUMENTS 5,781,638 A * 7/1998 Hosaka ................ H04R 1/1016 381/322
10,820,084 B2 * 10/2020 Zalisk .................. H04R 1/1016
11,095,973 B1 * 8/2021 Zalisk .................. G10K 11/175
12,336,885 B2 6/2025 Smith
2001/0017230 A1 8/2001 Brimhall et al.
2015/0382094 A1 * 12/2015 Grinker ................ H04R 1/1058 381/380
2016/0066110 A1 * 3/2016 Shennib ............... H04R 25/652 381/328
2018/0124531 A1 * 5/2018 Tourdot ............... H04R 25/604
2019/0007762 A1 1/2019 Paetsch et al.
(Continued)

FOREIGN PATENT DOCUMENTS

JP H0965475 A * 3/1997 ........... H04R 1/1016
WO WO-0141503 A2 * 6/2010 ........... H04R 25/602
(Continued)

*Primary Examiner* — Qin Zhu
(74) *Attorney, Agent, or Firm* — Luedeka Neely. P.C.

(57) ABSTRACT

A universal-fit hearing protection device includes an electronics module, sound tube interface, concha shell, and ear tip. The sound tube interface includes a sleeve and a nozzle extending from the sleeve. The sleeve, which slidably attaches to the electronics module, includes a sound tube opening aligned with a sound port on the electronics module. The nozzle includes a sound tube extending therethrough. The concha shell includes a cavity and an aperture in communication with the cavity. The cavity receives the electronics module and the attached sound tube interface. The aperture in the cavity receives the nozzle when the electronics module and sound tube interface are in the cavity. The ear tip includes a tubular core that receives the nozzle, and the compliant outer structure disposed around the tubular core that is received within an ear canal of the user. The nozzle may be an integral part of the electronics module.

18 Claims, 10 Drawing Sheets

(56) References Cited

U.S. PATENT DOCUMENTS

| | | | | |
|---|---|---|---|---|
| 2022/0021984 | A1 | 1/2022 | Lim et al. | |
| 2022/0239999 | A1 | 7/2022 | Kirkpatrick | |
| 2023/0224617 | A1* | 7/2023 | Bacon | H04R 1/1016 381/328 |
| 2023/0351064 | A1 | 11/2023 | Shahar et al. | |
| 2024/0414467 | A1* | 12/2024 | Mosgrove | H04R 1/1016 |
| 2026/0039992 | A1 | 2/2026 | Briggs et al. | |

FOREIGN PATENT DOCUMENTS

| | | | | |
|---|---|---|---|---|
| WO | WO-2023096641 A1 | * | 6/2023 | H04R 1/105 |
| WO | WO-2024208662 A1 | * | 10/2024 | H04R 1/1075 |
| WO | WO-2024254449 A1 | * | 12/2024 | H04R 1/1016 |

* cited by examiner

UNIVERSAL FITTING STRUCTURE FOR HEARING PROTECTION DEVICE

FIELD OF THE INVENTION

This invention relates to universal fit structures for hearing protection devices and hearing assistance devices worn in a user's concha and ear canal. More particularly, this invention relates to a user-customizable structure for providing a comfortable and effective fit for hearing protection devices and hearing assistance devices without the need for a custom earmold.

BACKGROUND OF THE INVENTION

Devices are currently available that combine hearing assistance and hearing protection for users. Examples of such devices are described in U.S. Pat. No. 12,069,435 (the '365 patent), the entire contents of which are incorporated herein by reference. These devices include an electronic component that is programmed to provide hearing assistance during when ambient sound levels are relatively low, and to activate fast compression to shut off sound amplification when a loud noise is detected, and to resume normal amplification after the loud noise ends. Such devices provide hearing protection in high noise level environments, such as in military, industrial, hunting, or loud musical settings.

To provide a maximum level of hearing protection in extreme environments, many of these devices include a custom-fit earmold for containing the electronic component. Such earmolds provide a very tight fit to the user's concha and ear canal. Although such earmolds are highly effective, they require precise measurements of the user's ear and custom molding based on the measurements, which can be expensive and time consuming.

What is needed, therefore, is a hearing aid/protection device that provides an adequately tight fit to the user's concha and ear canal using "off the shelf" universal-fit components that do not require custom measurement/molding procedures.

SUMMARY OF THE INVENTION

The above and other needs are met by a universal-fit hearing protection device comprising an electronics module, a sound tube interface, a concha shell, and an ear tip. The electronics module contains electronics that incorporate digital signal processing to provide sound amplification and digital signal processing to provide fast compression programming to shut off sound amplification to protect a user of the device when a loud noise is detected. The electronics module has a sound port disposed in the output end of the electronics module. The sound port configured to propagate sound generated by the electronics. The sound tube interface, which is configured to be attached to the electronics module, includes a sleeve portion and a nozzle portion. The sleeve portion is configured to be slidably attachable to and removable from the output end of the electronics module. The sleeve portion includes a sound tube opening that is aligned with the sound port of the electronics module when the sound tube interface is attached to the electronics module. The nozzle portion, which extends outward from the sleeve portion, includes a sound tube that extends through the nozzle portion and is in communication with the sound tube opening in the sleeve portion. The concha shell is configured to be received in an ear concha of the user. The concha shell comprises a cavity and an aperture in communication with the cavity. The cavity is configured to receive at least a portion of the electronics module and the sound tube interface attached to the electronics module. The aperture is configured to receive the nozzle portion of the sound tube interface when the electronics module and sound tube interface are received in the cavity. The ear tip is configured to be attached to the nozzle portion of the sound tube interface. The ear tip comprises a tubular core and a compliant outer structure. The tubular core is configured to receive the nozzle portion of the sound tube interface. The compliant outer structure is disposed around the tubular core and is configured to be received within an ear canal of the user.

In some embodiments, the electronics module includes a ridge protruding from an outer surface of the electronics module adjacent the output end thereof, and the sleeve portion of the sound tube interface includes an internal channel configured to receive the ridge when the sound tube interface is attached to the electronics module.

In some embodiments, the nozzle portion of the sound tube interface has external threads, and the tubular core of the ear tip has internal threads corresponding to the external threads of the nozzle portion.

In some embodiments, the nozzle portion of the sound tube interface includes an interference fit structure, and the tubular core of the ear tip is configured to engage with the interference fit structure of the nozzle portion.

In some embodiments, the sleeve portion and the nozzle portion of the sound tube interface comprise a one-piece integral structure.

In some embodiments, the concha shell is shaped and dimensioned to provide a universal fit that is applicable to more than one user.

In some embodiments, the concha shell is formed from a compliant material, such as silicone.

In some embodiments, the compliant outer structure of the ear tip is shaped and dimensioned to provide a universal fit that is applicable to more than one user.

In some embodiments, the compliant outer structure of the ear tip comprises viscoelastic foam.

Some embodiments are directed to a method for assembling the universal-fit hearing protection device comprising the following steps:

(a) sliding the sleeve portion of the sound tube interface onto the output end of the electronics module such that the sound tube opening of the sleeve portion is aligned with the sound port of the electronics module;

(b) inserting the electronics module with the sound tube interface attached thereto into the cavity of the concha shell until the nozzle portion of the sound tube interface protrudes from the aperture in the concha shell; and (c) securely engaging the tubular core of the ear tip with the protruding nozzle portion of the sound tube interface.

In some embodiments in which the nozzle portion of the sound tube interface has external threads, and the tubular core of the ear tip has internal threads corresponding to the external threads of the nozzle portion, step (c) of the method comprises rotating the ear tip to engage the internal threads of the tubular core with the external threads of the nozzle portion, and continuing to rotate the ear tip until the ear tip abuts against the concha shell and is securely attached.

In some embodiments in which the nozzle portion of the sound tube interface includes an interference fit structure, and the tubular core of the ear tip is configured to engage with the interference fit structure of the nozzle portion of the sound tube interface, step (c) of the method comprises pressing the ear tip to engage the tubular core with the interference fit structure of the nozzle portion, and continuing to press the ear tip until the ear tip abuts against the concha shell and is securely attached.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION OF THE INVENTION

Figure 7A:
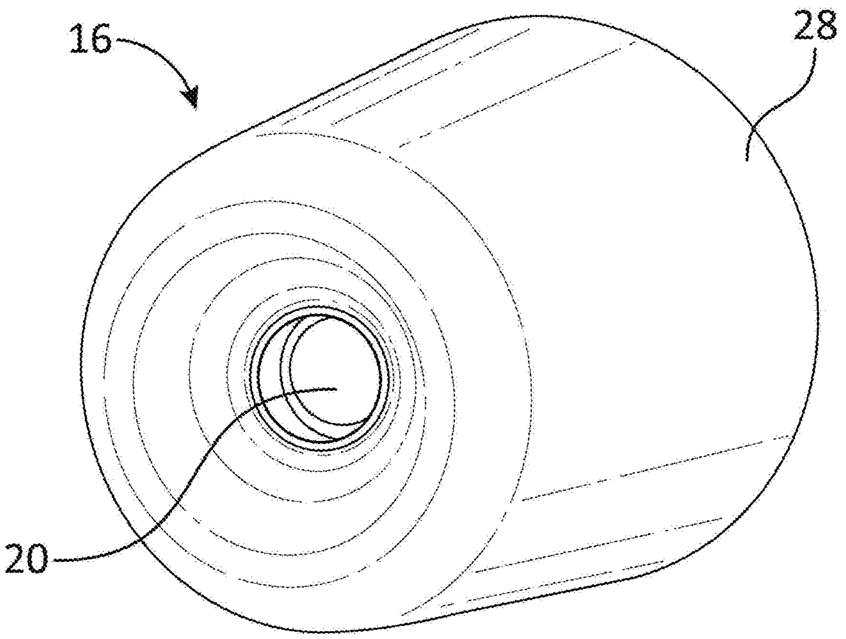
FIGS. 7A and 7B depict the ear tip portion of the universal-fit hearing protection/assistance device according to a preferred embodiment.
Figure 7B:
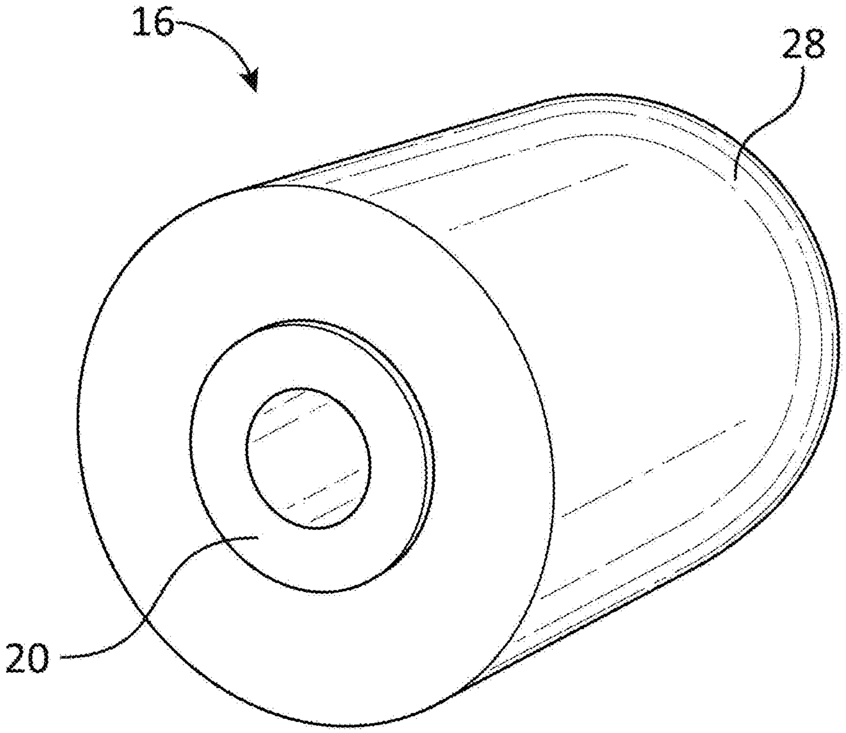
Figure 8A:
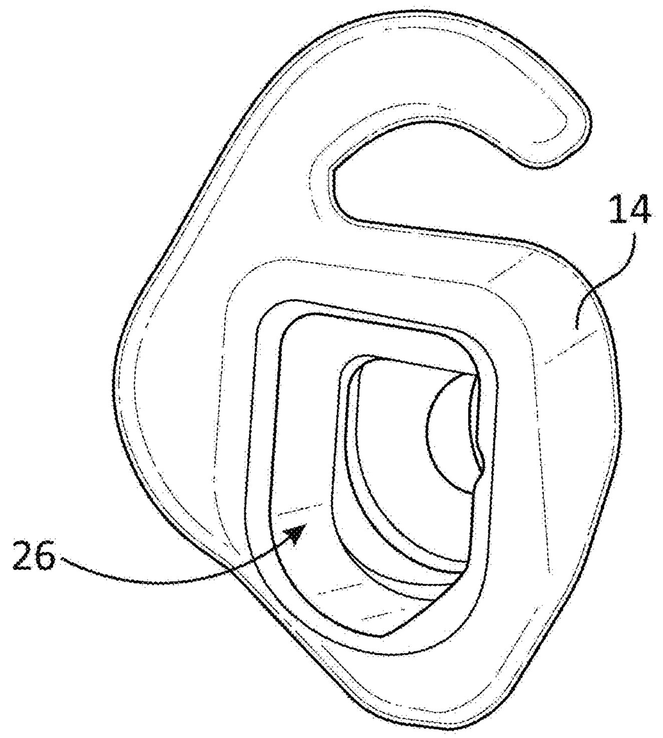
FIGS. 8A and 8B depict the concha shell portion of the universal-fit hearing protection/assistance device according to a preferred embodiment.
Figure 8B:
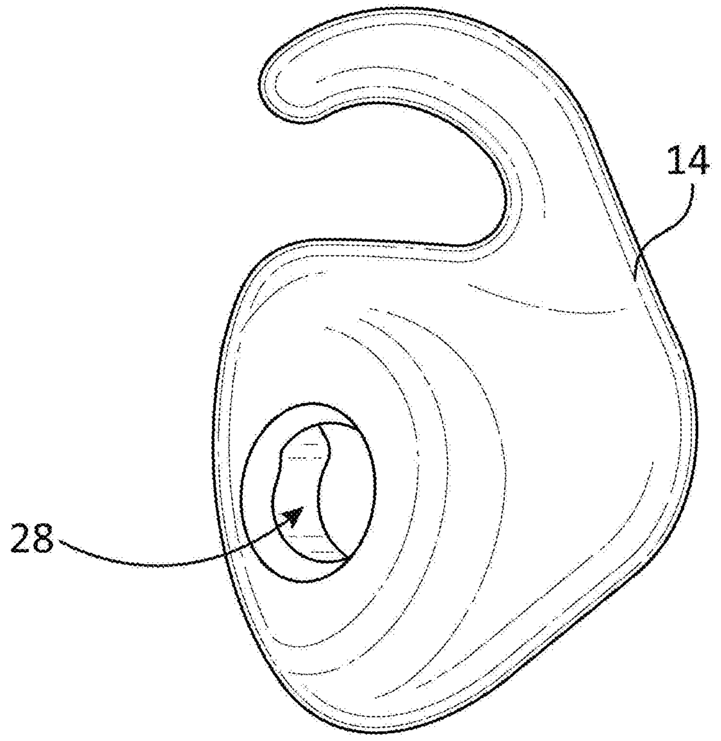
Figure 9A:
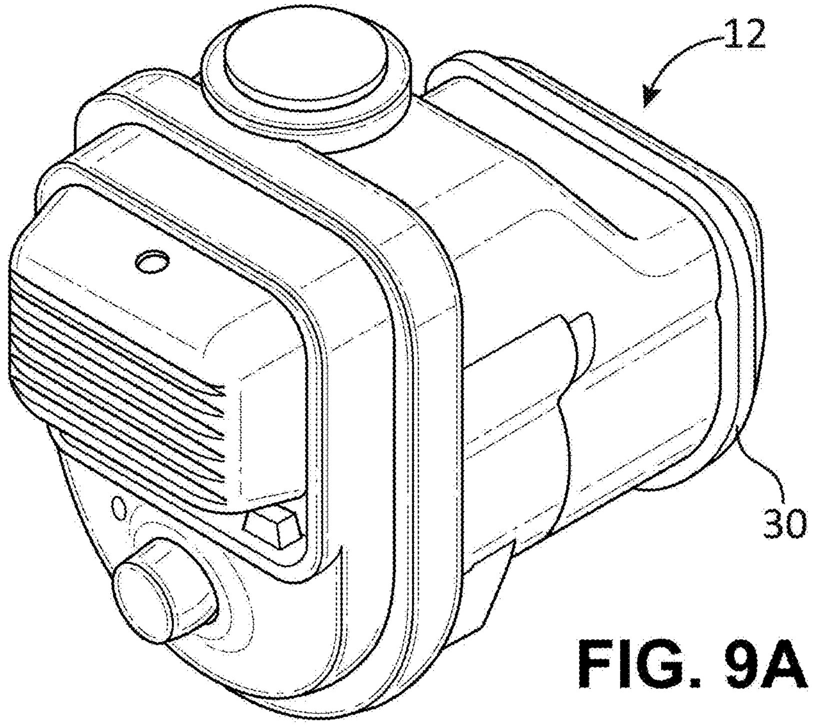
FIGS. 9A and 9B depict the electronics module of the universal-fit hearing protection/assistance device according to a preferred embodiment.
Figure 9B:
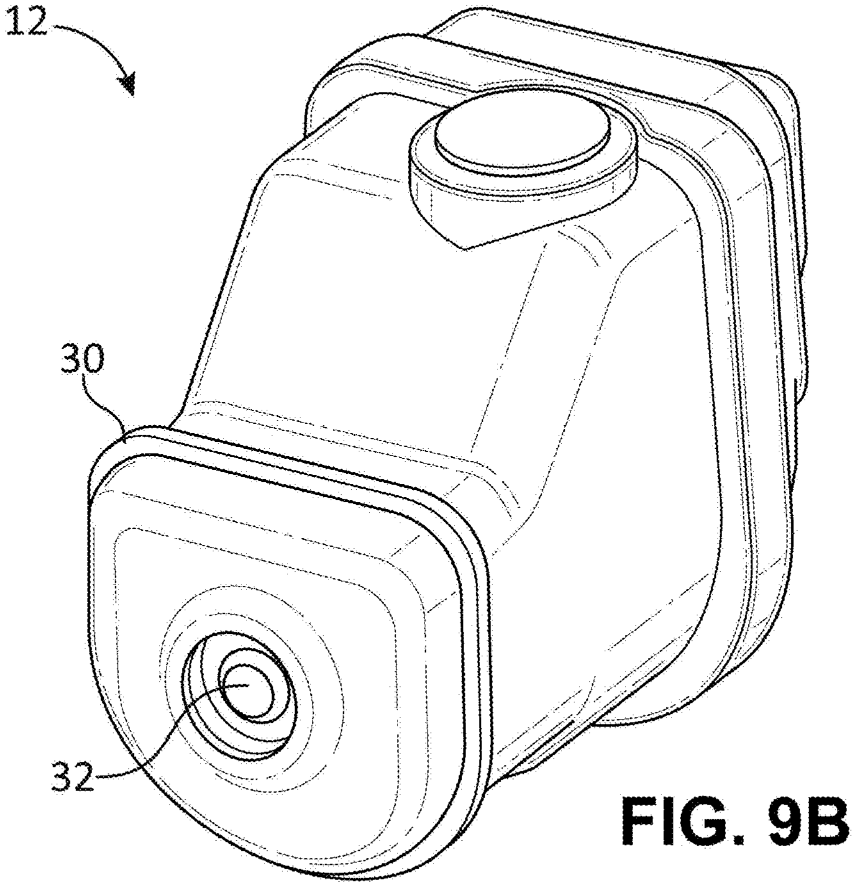

As shown in FIGS. 1A-1C and 2A-2B, a universal-fit hearing protection and assistance device 10 includes an electronics module 12, a concha shell 14, an ear tip 16, and a sound tube interface 18. The electronics module 12 (also shown in FIGS. 9A-9B) provides hearing protection/assistance functions, and communication functions in some embodiments, as described in the '365 patent. The concha shell 14 (also shown in FIGS. 8A-8B) may be molded from silicone or some other similarly compliant material. The concha shell 14 has an internal cavity 26 with an interference fit structure for receiving and securing the electronics module 12 therein. In a preferred embodiment, the ear tip 16 (also shown in FIGS. 7A-7B) comprises a Comply™ canal ear tip having a soft memory foam outer structure that surrounds a tapered cylindrical core 20.

Figure 6A:
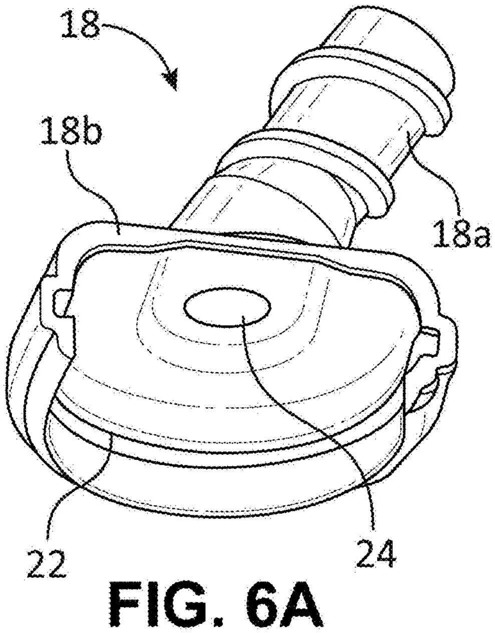
FIGS. 6A, 6B, and 6C depict the nozzle portion of the universal-fit hearing protection/assistance device according to the first embodiment.
Figure 6B:
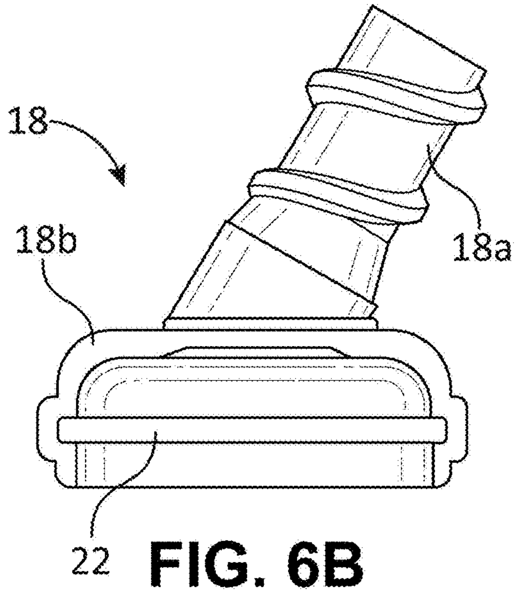
Figure 6C:
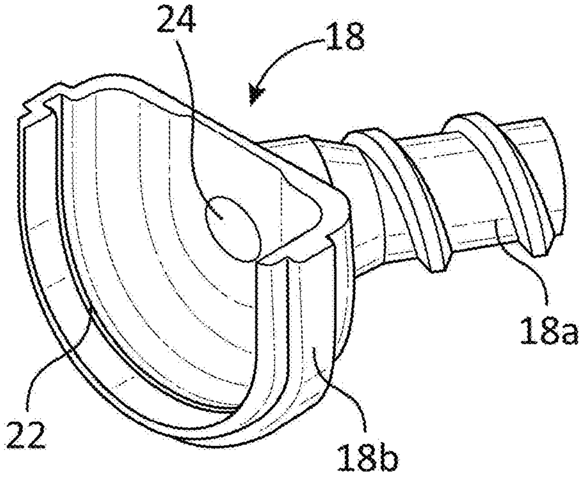

As depicted in FIGS. 4A-4G, 5, and 6A-6C, the sound tube interface 18 includes a sleeve portion 18*b* and a nozzle portion 18*a* extending therefrom. Extending the length of the nozzle portion 18*a* is a sound tube 34 that is in communication with a sound tube opening 24 in the sleeve portion 18*b*. The sleeve portion 18*b* is configured to be slidably attachable to and removable from the output end of the electronics module 12. As shown in FIGS. 6A-6C, the sleeve portion 18*b* includes an internal channel 22 that is configured to receive a ridge 30 on the outer surface of the electronics module 12. This structure prevents the sleeve portion 18*b* from being pulled away from the electronics module 12 in the axial direction. When the sleeve portion 18*b* of the sound tube interface 18 is attached to the electronics module 12, as shown in FIGS. 4A-4G and 5, the sound tube opening 24 is aligned with a sound port 32 on the electronics module 12. This allows sound emitting from the sound port 32 to travel into the sound tube opening 24 and through the sound tube 34 within the nozzle portion 18*a*.

Figure 1A:
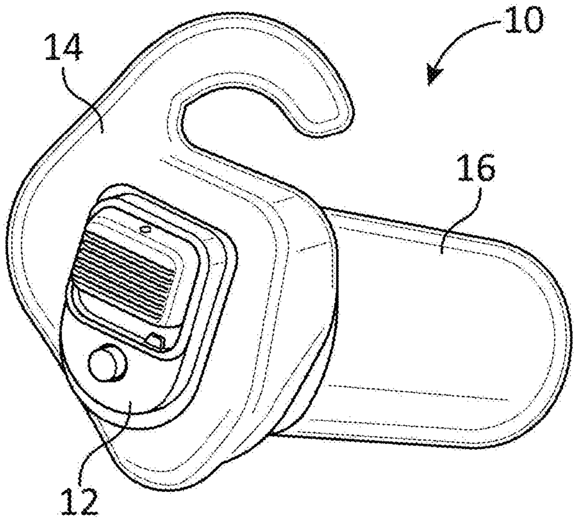
FIGS. 1A, 1B, and 1C depict a universal-fit hearing protection/assistance device according to an embodiment described herein.
Figure 1B:
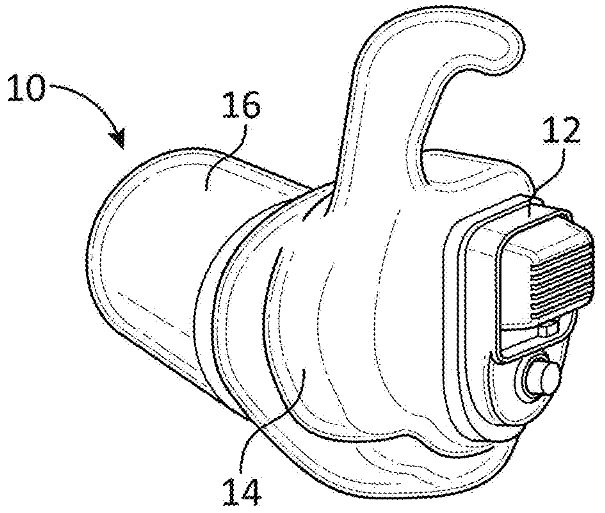
Figure 1C:
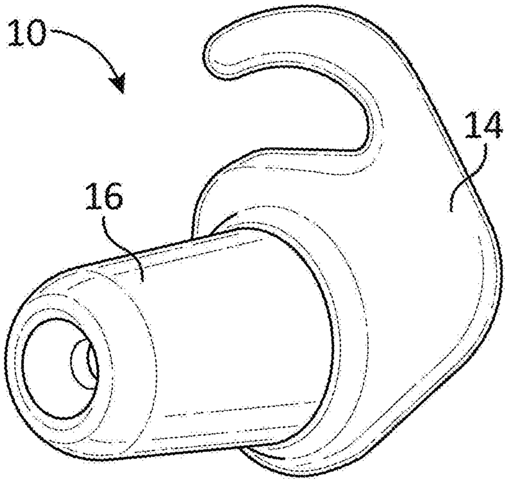
Figure 2A:
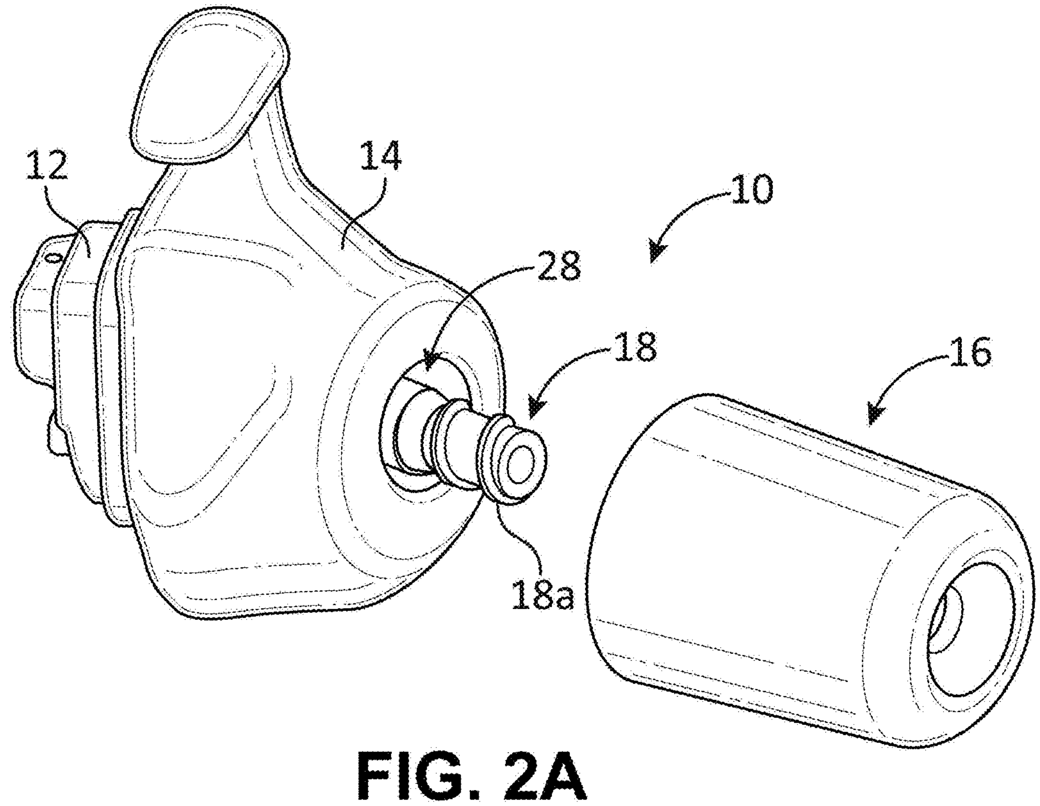
FIGS. 2A and 2B depict the universal-fit hearing protection/assistance device with the ear tip portion detached.
Figure 2B:
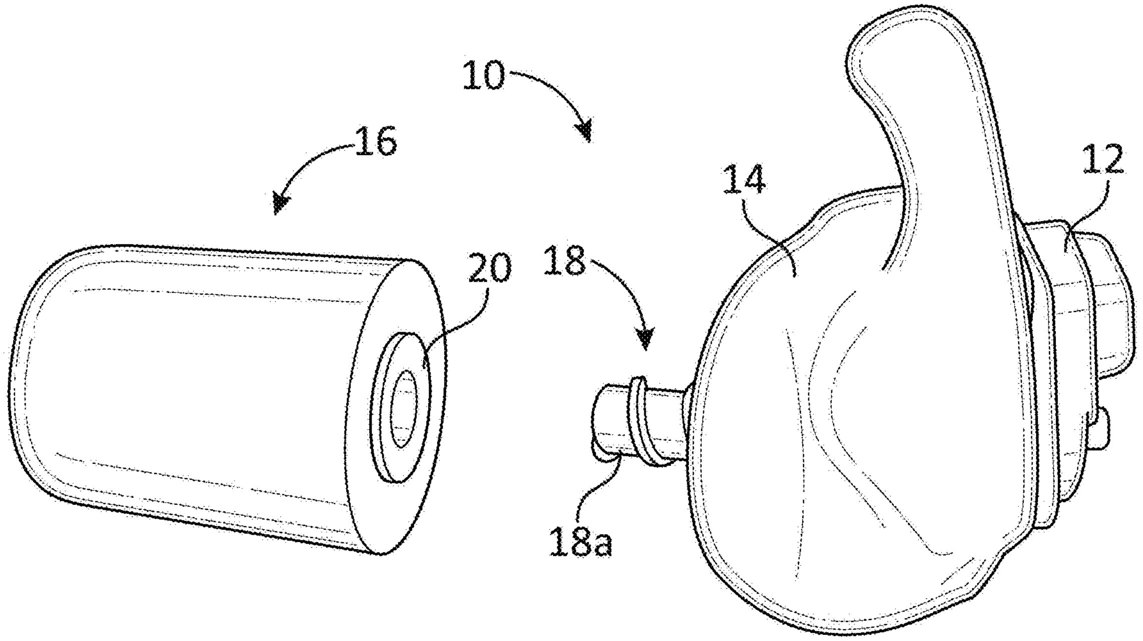
Figure 3A:
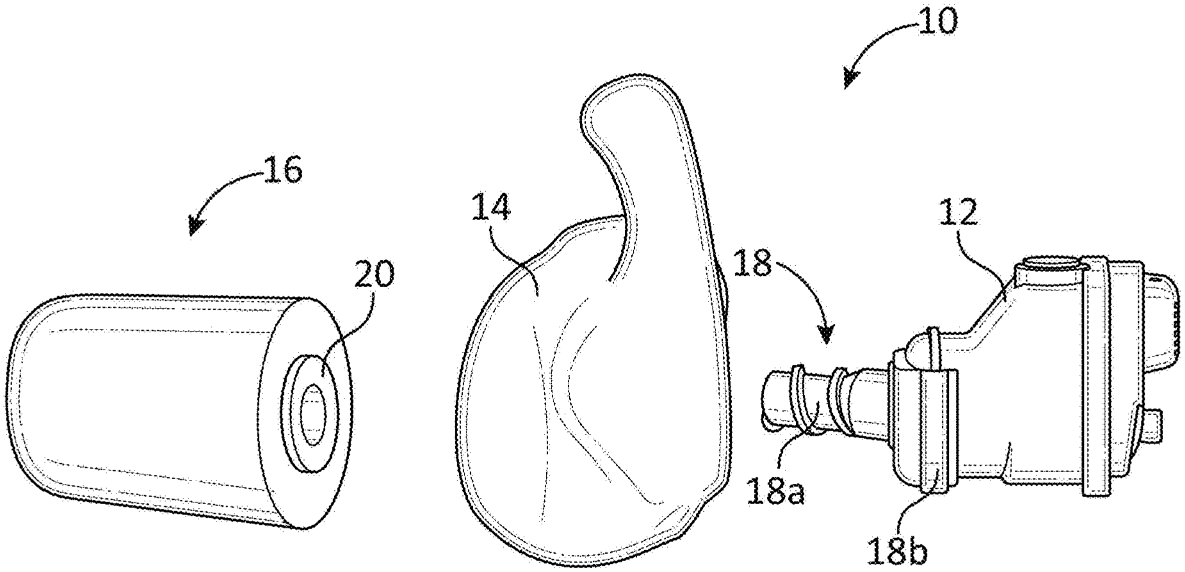
FIGS. 3A and 3B depict the universal-fit hearing protection/assistance device with the ear tip portion detached, and the electronics module and nozzle portion removed from the concha shell.
Figure 3B:
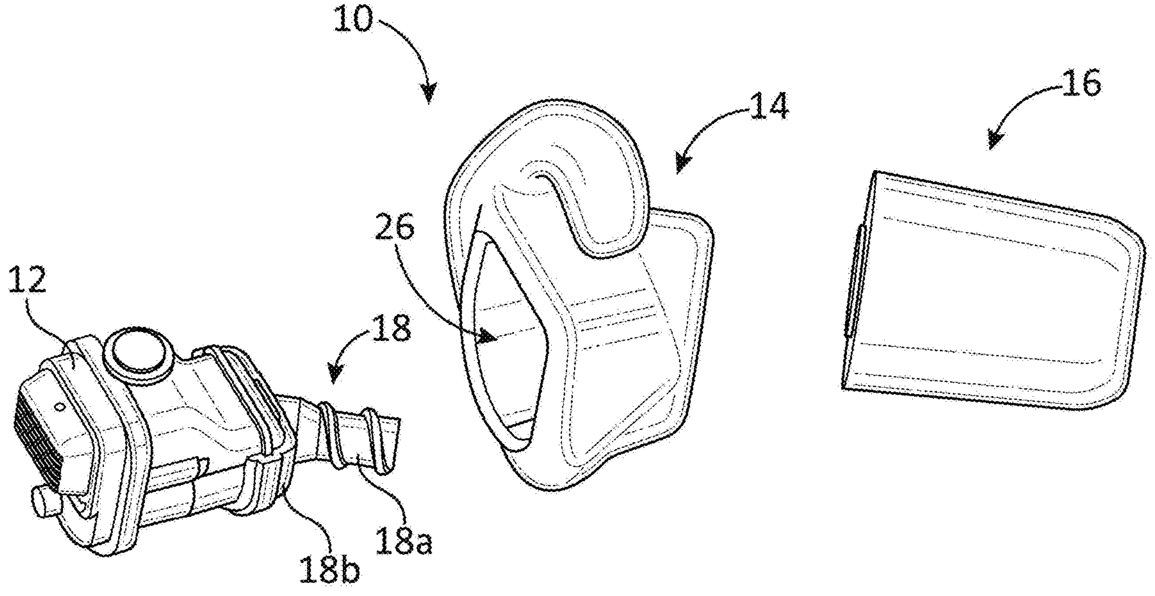
Figure 4A:
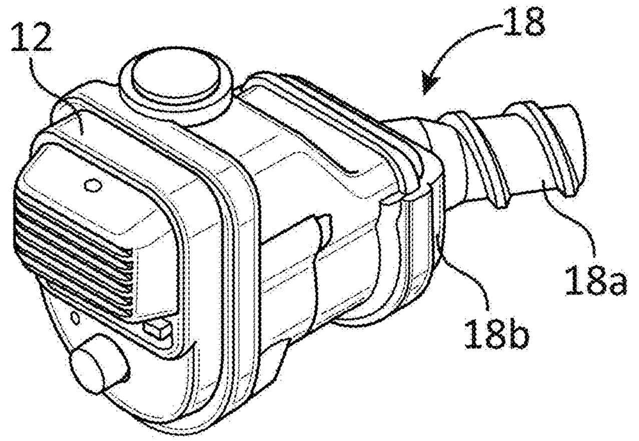
FIGS. 4A-4G depict the electronics module and nozzle portion of the universal-fit hearing protection/assistance device according to a first embodiment.
Figure 4B:
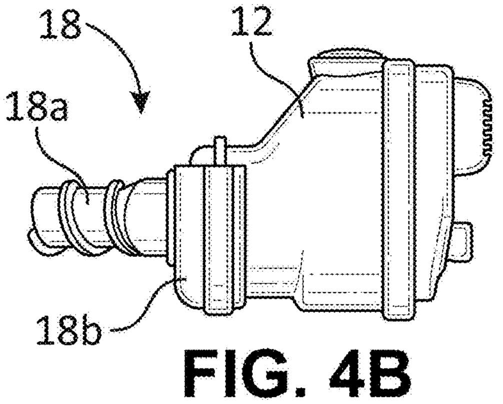
Figure 4C:
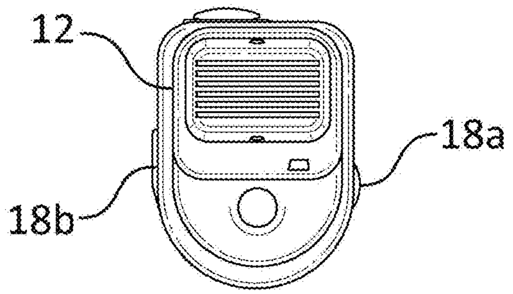
Figure 4D:
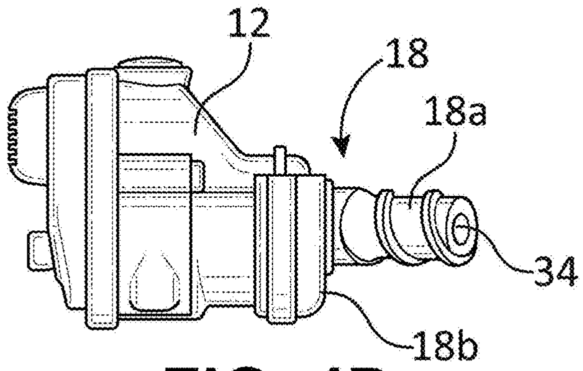
Figure 4E:
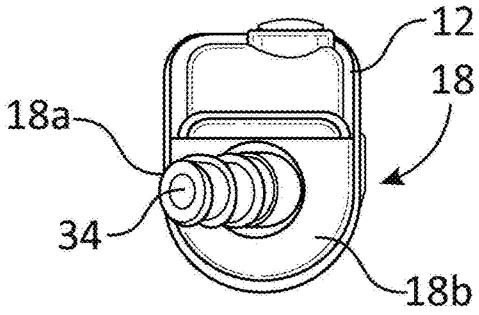
Figure 4F:
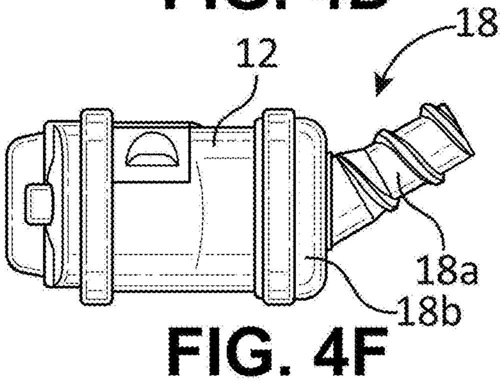
Figure 4G:
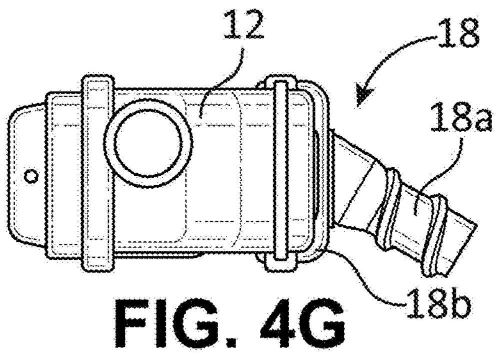
Figure 5:
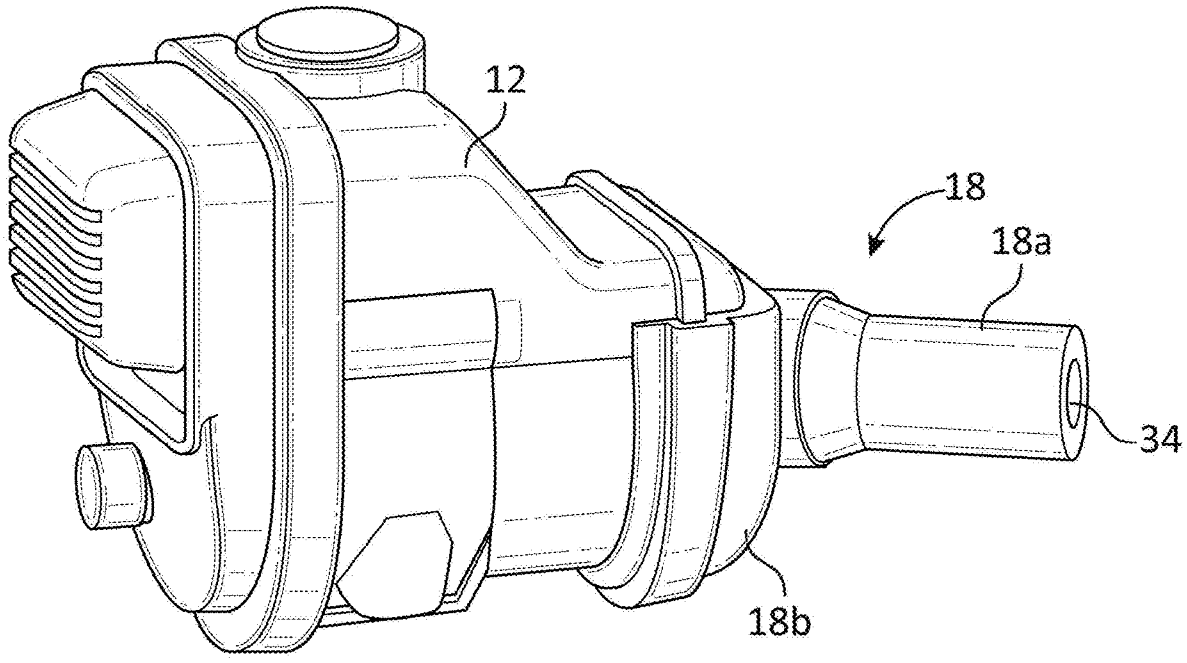
FIG. 5 depicts the electronics module and nozzle portion of the universal-fit hearing protection/assistance device according to a second embodiment.

In one embodiment, the cylindrical core 20 of the ear tip 16 has internal threads that match external threads on the nozzle 18*a* of the sound tube interface 18. As shown in FIG. 2A, when the electronics module 12 is inserted into the concha shell 14, the nozzle 18*a* extends through an aperture 28 in the concha shell 14. In an alternative embodiment depicted in FIG. 5, the nozzle 18*a* is not threaded, but has a smooth outer surface that is received into a corresponding smooth internal surface of the cylindrical core 20 of the ear tip 16. In this alternative embodiment, the ear tip 16 is secured to the nozzle 18*a* by an interference fit between the outer surface of the nozzle 18*a* and the internal surface of the cylindrical core 20.

Figure 10A:
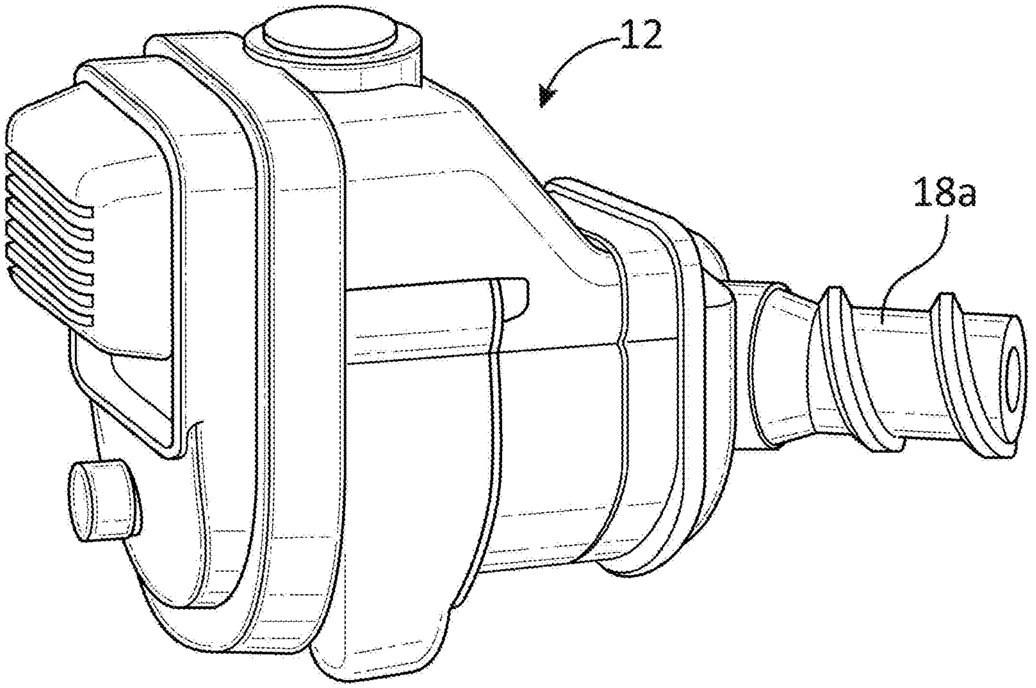
FIGS. 10A and 10B depict the electronics module of the universal-fit hearing protection/assistance device with an integrated nozzle according to an alternative embodiment.
Figure 10B:
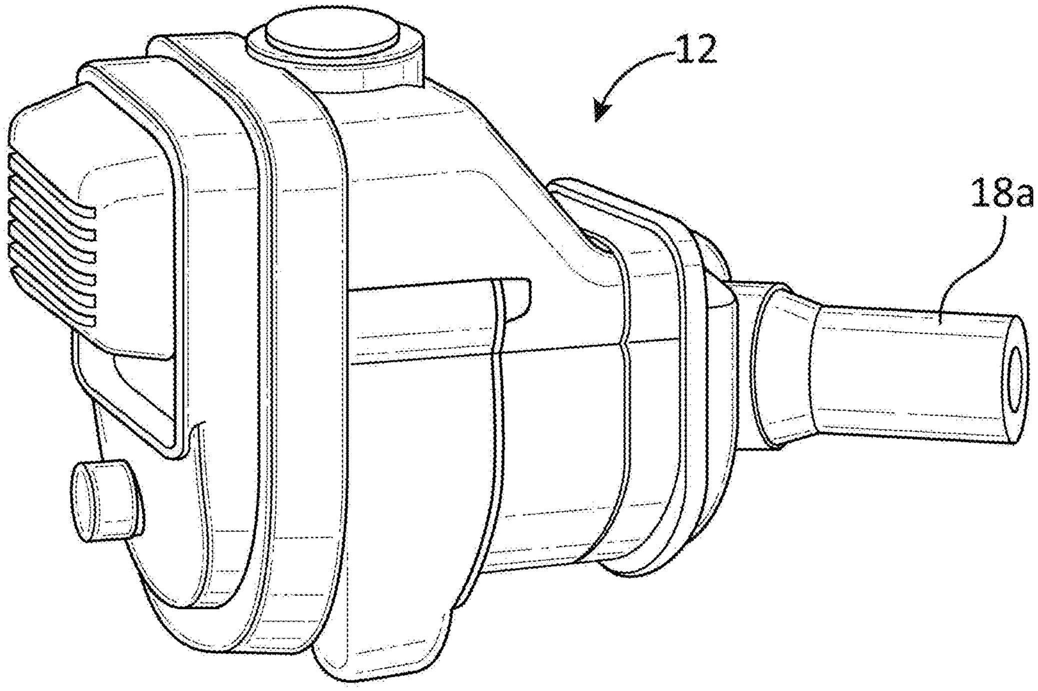

In an alternative embodiment, the nozzle 18*a* is integrated into the housing of the electronics module 12, as depicted in FIGS. 10A and 10B. Since the nozzle 18*a* is an integral part of the electronics module 12, it is not removable, and there is no need for a separate sleeve portion. In this embodiment, one version of the electronics module 12 has a nozzle 18*a* that is threaded, and another version has a nozzle 18*a* with an interference fit structure for attachment of the ear tip 16.

In some embodiments, the user may receive the universal-fit hearing protection/assistance device 10 as a disassembled kit that includes the electronics module 12, two versions of the sound tube interface 18 (threaded and interference-fit), multiple concha shells 14 in various sizes, and multiple ear tips 16 in various sizes. The user may then assemble the parts in various combinations to determine the most effective and comfortable fit. A process for assembling the parts of the universal-fit hearing protection device may include:

- sliding the sleeve portion 18*b* of the selected sound tube interface 18 onto the output end of the electronics module 12 so that the sound tube opening 24 of the sound tube interface 18 is aligned with the sound port 32 of the electronics module 12;
- inserting the electronics module 12 with the sound tube interface 18 attached thereto into the cavity 26 of the concha shell 14 until the nozzle portion 18*a* of the sound tube interface 18 is protruding from the aperture 28 in the concha shell 14; and
- securely engaging the tubular core 20 of the ear tip 16 with the protruding nozzle portion 18*a* of the sound tube interface 18.

When using the threaded version of the sound tube interface 18, the step of securely engaging the ear tip 16 to the sound tube interface 18 comprises rotating the ear tip 16 to engage the internal threads of the tubular core 20 with the external threads of the nozzle portion 18*a*, and continuing to rotate the ear tip 16 until it abuts against the concha shell 14 and is securely attached. When using the interference-fit version of the sound tube interface 18, the step of securely engaging the ear tip 16 to the sound tube interface 18 pressing the ear tip 16 to engage the tubular core 20 with the interference-fit structure of the nozzle portion 18*a*, and continuing to press the ear tip 16 until it abuts against the concha shell 14 and is securely attached.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A universal-fit hearing protection device comprising:

an electronics module containing electronics that incorporate one or both of digital signal processing to provide sound amplification and digital signal processing to provide fast compression programming to shut off sound amplification to protect a user of the device when a loud noise is detected, the electronics module having a sound port disposed in an output end of the electronics module, the sound port configured to propagate sound generated by the electronics;

a sound tube interface configured to be attached to the electronics module, the sound tube interface comprising:

a sleeve portion configured to be slidably attachable to and removable from the output end of the electronics module, the sleeve portion including a sound tube opening that is aligned with the sound port of the electronics module when the sound tube interface is attached to the electronics module; and a nozzle portion extending outward from the sleeve portion, the nozzle portion including a sound tube that extends through the nozzle portion and is in communication with the sound tube opening in the sleeve portion;

a concha shell configured to be received in an ear concha of the user, the concha shell comprising:

a cavity configured to receive at least a portion of the electronics module and the sound tube interface attached to the electronics module; and an aperture in communication with the cavity, the aperture configured to receive the nozzle portion of the sound tube interface when the electronics module and sound tube interface are received in the cavity; and an ear tip configured to be attached to the nozzle portion of the sound tube interface, the ear tip comprising:

a tubular core configured to receive the nozzle portion of the sound tube interface; and a compliant outer structure disposed around the tubular core, the compliant outer structure configured to be received within an ear canal of the user.

2. The universal-fit hearing protection device of claim 1 wherein the electronics module includes a ridge protruding from an outer surface of the electronics module adjacent the output end thereof, and the sleeve portion of the sound tube interface includes an internal channel configured to receive the ridge when the sound tube interface is attached to the electronics module.

3. The universal-fit hearing protection device of claim 1 wherein the nozzle portion of the sound tube interface has external threads, and the tubular core of the ear tip has internal threads corresponding to the external threads of the nozzle portion.

4. The universal-fit hearing protection device of claim 1 wherein the nozzle portion of the sound tube interface includes an interference fit structure, and the tubular core of the ear tip is configured to engage with the interference fit structure of the nozzle portion.

5. The universal-fit hearing protection device of claim 1 wherein the sleeve portion and the nozzle portion of the sound tube interface comprise a one-piece integral structure.

6. The universal-fit hearing protection device of claim 1 wherein the concha shell is shaped and dimensioned to provide a universal fit that is applicable to more than one user.

7. The universal-fit hearing protection device of claim 1 wherein the concha shell is formed from a compliant material.

8. The universal-fit hearing protection device of claim 1 wherein the concha shell is formed from silicone.

9. The universal-fit hearing protection device of claim 1 wherein the compliant outer structure of the ear tip is shaped and dimensioned to provide a universal fit that is applicable to more than one user.

10. The universal-fit hearing protection device of claim 1 wherein the compliant outer structure of the ear tip comprises viscoelastic foam.

11. A method for assembling the universal-fit hearing protection device of claim 1 comprising:

(a) sliding the sleeve portion of the sound tube interface onto the output end of the electronics module such that the sound tube opening of the sleeve portion is aligned with the sound port of the electronics module;

(b) inserting the electronics module with the sound tube interface attached thereto into the cavity of the concha shell until the nozzle portion of the sound tube interface protrudes from the aperture in the concha shell; and (c) securely engaging the tubular core of the ear tip with the protruding nozzle portion of the sound tube interface.

12. The method of claim 11 wherein the nozzle portion of the sound tube interface has external threads, and the tubular core of the ear tip has internal threads corresponding to the external threads of the nozzle portion, and wherein step (c) comprises rotating the ear tip to engage the internal threads of the tubular core with the external threads of the nozzle portion, and continuing to rotate the ear tip until the ear tip abuts against the concha shell and is securely attached.

13. The method of claim 11 wherein the nozzle portion of the sound tube interface includes an interference fit structure, and the tubular core of the ear tip is configured to engage with the interference fit structure of the nozzle portion of the sound tube interface, and wherein step (c) comprises pressing the ear tip to engage the tubular core with the interference fit structure of the nozzle portion, and continuing to press the ear tip until the ear tip abuts against the concha shell and is securely attached.

14. A universal-fit hearing protection device comprising:

an electronics module containing electronics that incorporate one or both of digital signal processing to provide sound amplification and digital signal processing to provide fast compression programming to shut off sound amplification to protect a user of the device when a loud noise is detected, the electronics module having:

a sound port disposed in an output end of the electronics module, the sound port configured to propagate sound generated by the electronics; and a ridge on an outer surface of the electronics module adjacent to the output end;

a sound tube interface configured to be attached to the electronics module, the sound tube interface comprising:

a sleeve portion configured to be slidably attachable to and removable from the output end of the electronics module, the sleeve portion including:

a sound tube opening that is aligned with the sound port of the electronics module when the sound tube interface is attached to the electronics module; and an internal channel configured to receive the ridge on the outer surface electronics module when the sound tube interface is attached to the electronics module; and a nozzle portion extending outward from the sleeve portion, the nozzle portion including a sound tube that extends through the nozzle portion and is in communication with the sound tube opening in the sleeve portion, wherein the sleeve portion and the nozzle portion of the sound tube interface comprise a one-piece integral structure;

a concha shell formed from a compliant material and configured to be received in an ear concha of the user, the concha shell comprising:

a cavity configured to receive at least a portion of the electronics module and the sound tube interface attached to the electronics module; and an aperture in communication with the cavity, the aperture configured to receive the nozzle portion of the sound tube interface when the electronics module and sound tube interface are received in the cavity, wherein the concha shell is shaped and dimensioned to provide a universal fit that is applicable to more than one user; and an ear tip configured to be attached to the nozzle portion of the sound tube interface, the ear tip comprising:

a tubular core configured to receive the nozzle portion of the sound tube interface; and a compliant outer structure disposed around the tubular core, the compliant outer structure configured to be received within an ear canal of the user, wherein the compliant outer structure is shaped and dimensioned to provide a universal fit that is applicable to more than one user.

15. The universal-fit hearing protection device of claim 14 wherein the nozzle portion of the sound tube interface has external threads, and the tubular core of the ear tip has internal threads corresponding to the external thread of the nozzle portion.

16. The universal-fit hearing protection device of claim 14 wherein the nozzle portion of the sound tube interface includes an interference fit structure, and the tubular core of the ear tip is configured to engage with the interference fit structure of the nozzle portion.

17. The universal-fit hearing protection device of claim 14 wherein the concha shell is formed from silicone.

18. A method for assembling the universal-fit hearing protection device of claim 14 comprising:

(a) sliding the sleeve portion of the sound tube interface onto the output end of the electronics module such that the sound tube opening of the sleeve portion is aligned with the sound port of the electronics module;

(b) inserting the electronics module with the sound tube interface attached thereto into the cavity of the concha shell until the nozzle portion of the sound tube interface protrudes from the aperture in the concha shell; and (c) securely engaging the tubular core of the ear tip with the protruding nozzle portion of the sound tube interface.

* * * * *